(12) United States Patent
Shimada et al.

(10) Patent No.: US 6,689,798 B2
(45) Date of Patent: Feb. 10, 2004

(54) BENZOFURAN DERIVATIVES

(75) Inventors: Shin'ichi Shimada, Shimotsuga-gun (JP); Shin Nomoto, Kawachi-gun (JP); Masayuki Okue, Shimotsuga-gun (JP); Ken'ichi Kimura, Hanamaki (JP); Junji Nakamura, Kawachi-gun (JP); Yoshikazu Ikeda, Shimotsuga-gun (JP); Takeko Takada, Utsunomiya (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/298,771

(22) Filed: Nov. 18, 2002

(65) Prior Publication Data

US 2003/0149079 A1 Aug. 7, 2003

Related U.S. Application Data

(63) Continuation of application No. PCT/JP01/04190, filed on May 18, 2001.

(30) Foreign Application Priority Data

May 18, 2000 (JP) ........................ 2000-146583

(51) Int. Cl.[7] ............... A61K 31/4427; C07D 405/14; C07D 405/04; C07D 409/14
(52) U.S. Cl. .............. 514/333; 546/256; 546/280.4; 546/283.7; 546/284.1; 514/337; 514/338
(58) Field of Search .............. 514/337, 333, 514/338; 546/284.1, 283.7, 280.4, 256

(56) References Cited

U.S. PATENT DOCUMENTS 3,678,062 A 7/1972 Bauer, et al.

FOREIGN PATENT DOCUMENTS

| EP | 0 445 073 | 9/1991 |
| JP | 1-213276 | 8/1989 |
| WO | WO 95/29907 | 11/1995 |

OTHER PUBLICATIONS

F. Messina, et al., Tetrahedron Letters, vol. 40, No. 40, pp. 7289–7292, "Chiral Azole Derivatives, 3[1]. Synthesis of the Enantiomers of the Potent Aromatase Inhibitor 1–[2–Benzofuranyl(4–Chlorophenyl)Methyl]–1H–Imidazole", 1999.

*Primary Examiner*—Charanjit S. Aulakh
(74) *Attorney, Agent, or Firm*—Oblon, Spivak, McClelland, Maier & Neustadt, P.C.

(57) ABSTRACT

The present invention provides novel benzofuran derivatives represented by the following formula (I) or salts thereof:

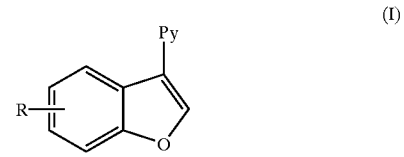

wherein Py is a 2-, 3-, or 4-pyridyl group and R is a substituted or unsubstituted phenyl group or a substituted or unsubstituted aromatic heterocyclic group.

The present invention also relates to inhibitors of steroid 17α-hydroxylase and/or steroid C17-20 lyase and pharmaceutical compositions containing a benzofuran derivative of the above formula (I), or the salt.

17 Claims, No Drawings

BENZOFURAN DERIVATIVES

RELATED APPLICATION

This application is a Continuation of PCT/JP01/04190 filed May 18, 2001, which claims priority to Japanese Patent Application No. 146583/2000 filed May 18, 2000, the entirety of which are incorporated herein by reference.

FIELD OF THE INVENTION

The present invention relates to novel benzofuran derivatives. The present invention also relates to inhibitors of steroid 17α-hydroxylase and/or steroid C17-20 lyase and pharmaceutical composition containing the novel benzofuran derivatives.

BACKGROUND OF THE INVENTION

In the formation of sex steroids in living bodies, 1)C21-steroids, such as a progesterone, are formed from cholesterol, 2)androgenic hormones, such as androstenedione and testosterone, which are C19-steroids, are synthesized from C21-steroids by steroid 17α-hydroxylase and/or steroid C17-20 lyase, and 3)estrogens, such as estrone and estradiol, which are C18-steroids, are synthesized from these C19-steroids as a substrate by aromatase enzymes. All these sex steroids are known to exhibit various activities.

If the steroid 17α-hydroxylase and/or steroid C 17-20 lyase or aromatase, which are enzymes synthesizing these sex steroids, are inhibited, in vivo formation of androgenic hormones and/or estrogens can be controlled. Thus, it is possible to prevent or treat various diseases, in which androgenic hormones or estrogens are involved as an exacerbation factor, such as prostate cancer, prostatic hypertrophy (prostatism), androgenic syndrome (masculinism), andromorphous baldness, breast cancer, mastopathy, uterine cancer, endometriosis, and ovarian cancer.

It is already revealed from numerous findings that these diseases relating to androgenic hormones, such as prostate cancer and prostatic hypertrophy, can be treated by reducing the amount of androgenic hormones in the blood. For example, conventionally decrease in the androgenic hormones was brought about by orchidectomy or adrenalectomy. A decrease in the androgenic hormones originating from the gonad gland by the administration of an LH-RH agonist, which is a kind of hypophysis hormone has been reported recently to exhibit treatment effects.

However, the above-mentioned evisceration is not only psychologically difficult to accept, but also may be accompanied by side effects caused by a decrease of mineral corticoid or glucocorticoid from the adrenal glands. The administration of an LH-RH agonist only inhibits synthesis of hormones of gonad gland origin and is not expected to decrease hormones originating from other organs such as the adrenal glands. In addition, a problem of "flare phenomenon" due to a temporary increase of hormones unique to the agonist has been indicated.

On the other hand, although anti-androgenic hormone agents antagonistic to androgenic hormone receptors have been developed, a recent report indicated a decrease in the effect of such an agent due to denaturing of the androgenic hormone receptors.

In view of this situation, development of a more effective agent for decreasing androgenic hormones is desired. It is possible to decrease greatly androgenic hormones by inhibiting steroid 17α-hydroxylase and/or steroid C17-20 lyase. Therefore, inhibition of these steroids is expected to exhibit high effects in the treatment of various diseases in which the androgenic hormones are involved, such as prostate cancer, prostatic hypertrophy, and masculinization disease. In addition, inhibition of steroid 17α-hydroxylase and/or steroid C17-20 lyase may result in interruption of estrogen synthesis.

Up to the present time, steroid compounds and non-steroid compounds have been known as inhibitors of steroid 17α-hydroxylase and/or steroid C17-20 lyase. Examples include non-steroid compounds such as imidazole derivatives disclosed in Japanese Patent Laid-open Application No. 64-85975 and azole derivatives having a condensed three-ring structure disclosed in WO 95/09157. However, because these compounds are not necessarily satisfactory in their effects, development of compounds exhibiting higher activity has been desired.

SUMMARY OF THE INVENTION

In view of the above situation, the inventors of the present invention have carried out extensive studies to discover substances inhibiting steroid 17α-hydroxylase and/or steroid C17-20 lyase. As a result, the inventors have found that a certain compound possessing a benzofuran skeleton exhibits potent inhibitory activity of steroid 17α-hydroxylase and/or steroid C17-20 lyase, as well as aromatase. Therefore, an object of the present invention is to provide novel benzofuran derivatives, which inhibit steroid 17α-hydroxylase and/or steroid C17-20 lyase.

Another object of the present invention is to provide novel steroid 17α-hydroxylase and/or steroid C 17-20 lyase inhibitors and pharmaceutical compositions.

The present invention relates to novel benzofuran derivatives. The compounds of the present invention exhibit potent inhibitory activity of steroid 17α-hydroxylase and/or steroid C17-20 lyase. They also inhibit aromatase. Due to its activity, the compounds of the present invention are useful as preventive and/or therapeutic agents for various diseases, in which androgenic hormones and estrogens are involved, such as prostate cancer, prostatic hypertrophy (prostatism), androgenic syndrome (masculinization), andromorphous baldness, breast cancer, mastopathy, uterine cancer, endometriosis, and ovarian cancer.

DETAILED DESCRIPTION OF THE INVENTION

Specifically, the present invention provides novel benzofuran derivatives represented by the following formula (I) or salts thereof:

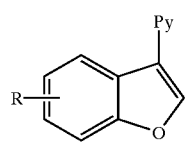

wherein Py is a 2-, 3-, or 4-pyridyl group and R is a substituted or unsubstituted phenyl group or a substituted or unsubstituted aromatic heterocyclic group.

As examples of the aromatic heterocyclic group in the compound of the present invention, heterocyclic groups containing a nitrogen atom and/or sulfur atom as the heteroatom, such as a pyridyl group or thienyl group can be given.

As the substituent on the phenyl group or aromatic heterocyclic group in the compound of the present invention, a hydroxyl group, lower alkyl group, lower alkyloxy group, halogen atom, carboxyl group, lower alkyloxycarbonyl group, carbamoyl group, amino group, amino group which may be substituted with one or two substituents selected from a lower alkyl group and lower acyl group, nitro group, or cyano group can be given. The lower alkyl group is a linear, branched, or cyclic hydrocarbon group having 1–7 carbon atoms, wherein the hydrocarbon group may be substituted with a halogen atom, hydroxyl group, alkyloxy group, amino group, amino group which may be substituted with one or two substituents selected from a lower alkyl group and lower acyl group, nitro group, or cyano group. The number of the substituents may be 1–3, and two of them in combination may form a lower alkylenedioxy group. Preferable substituents are a hydroxyl group, lower alkyloxy group, halogen atom, amino group, and carboxyl group, and particularly preferable groups are hydroxyl, methoxyl, fluorine atom, amino group, and carboxyl.

The following compounds can be given as specific examples of novel benzofuran derivatives represented by the formula (I) of the present invention:

(1) 3-[6-(4-methoxyphenyl)benzo[b]furan-3-yl]pyridine,
(2) 4-[3-(3-pyridyl)benzo[b]furan-6-yl]phenol,
(3) 3-[6-(4-fluorophenyl)benzo[b]furan-3-yl]pyridine,
(4) 3-[6-(3-fluorophenyl)benzo[b]furan-3-yl]pyridine,
(5) 3-[6-(3-methoxyphenyl)benzo[b]furan-3-yl]pyridine,
(6) 3-[3-(3-pyridyl)benzo[b]furan-6-yl]phenylamine,
(7) 3-[6-(3-pyridyl)benzo[b]furan-3-yl]pyridine,
(8) 3-[6-(1,3-benzodioxole-5-yl)benzo[b]furan-3-yl]pyridine,
(9) 3-(6-phenylbenzo[b]furan-3-yl)pyridine,
(10) 3-[6-(3,4-dimethoxyphenyl)benzo[b]furan-3-yl]pyridine,
(11) 3-[3-(3-pyridyl)benzo[b]furan-6-yl]phenol,
(12) 4-[3-(3-pyridyl)benzo[b]furan-6-yl]- 1,2-benzenediol,
(13) 3-[6-(3-thienyl)benzo[b]furan-3-yl]pyridine.

In addition to the above-mentioned compounds, the derivatives of the present invention include salts formed from these compounds and an acid or a base. As acid addition salts, for example, salts with a mineral acid, such as a hydrochloride, hydrobromide, hydroiodide, sulfate, nitrate, and phosphate, and salts with an organic acid, such as a formate, acetate, propionate, oxalate, malonate, succinate, fumarate, maleate, lactate, malate, citrate, tartrate, carbonate, picrate, methanesulfonate, and glutamate can be given. As salts with a base, for example, inorganic salts, such as a sodium salt, potassium salt, magnesium salt, calcium salt, and aluminium salt; organic salts, such as a lower alkylamine salt and lower alcoholic amine salt; salts with a basic amino acid such as lysine salts, arginine salts, and ornithine salts; ammonium salts; and the like can be given. In addition, the compounds of the present invention may form a hydrate or a solvate with a lower alcohol and the like.

The compounds (I) of the present invention can be prepared according to the process shown by the following reaction formula (1), for example.

In the following schematic reaction formula for the preparation of the compounds of the present invention, each symbol used in the compounds is the same as those previously described.

Reaction formula (1):

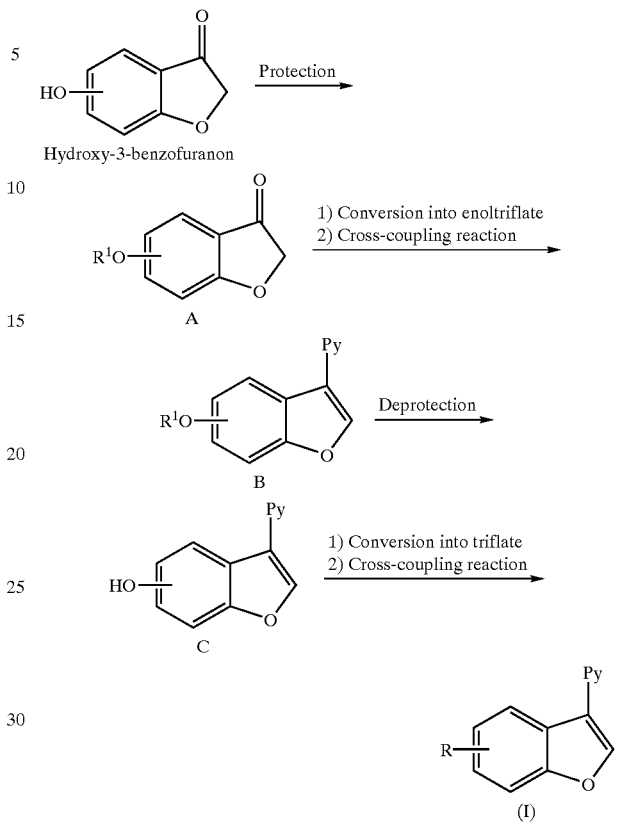

The hydroxyl group in hydroxy-3-benzofuranone is protected to prepare compound A. Then, after converting compound A into an enoltriflate, compound B is prepared by a cross-coupling reaction using a pyridyl borane derivative and a transition metal catalyst. The protective group is removed from compound B by a deprotecting reaction to prepare compound C, which is then converted into a triflate, followed by a cross-coupling reaction using various types of aryl boronic acid, aryl boronic acid ester, or borane derivative and a transition metal catalyst, thereby obtaining the objective compound (I). $R^1$ in the above reaction formula means a protective group for the hydroxyl group, and an aryl in the cross-coupling reaction indicates a substituted or unsubstituted phenyl group or a substituted or unsubstituted aromatic heterocyclic group. Py represents a 2-, 3-, or 4-pyridyl group. R represents a substituted or unsubstituted phenyl group or a substituted or unsubstituted aromatic heterocyclic group. As required, a substituent on the phenyl group or aromatic heterocyclic group represented by R is modified to obtain the objective compound. Here, example modifications of the substituent include dealkylation of an alkyl ether, acylation or alkylation of a hydroxyl group or amino group, and the like.

In an alternative method of obtaining compound B, compound A is converted into an enoltriflate, followed by a cross-coupling reaction using a boronating agent such as a tetra-alcoholate diboronic acid (bis(pinacolate) diboronic acid, for example) and a transition metal catalyst, to obtain a benzo[b]furan-3-boronic acid ester derivative. This compound is then subjected to a cross-coupling reaction using a sulfate derivative, such as various halogenated pyridine or hydroxy pyridine ("halogen" includes Cl, Br, or I, and "sulfate" includes an ester of methanesulfonic acid, trifluoromethane sulfonic acid or the like, for example) and a transition metal catalyst to prepare compound B. The reaction is shown in the following reaction formula (2).

Reaction formula (2):

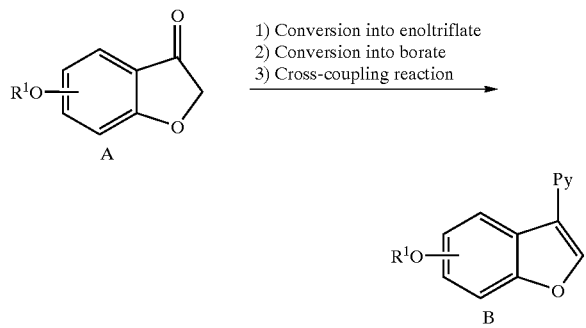

Compound B can also be obtained by a condensation-cyclization reaction of a dihydroxybenzene derivative D, the hydroxyl group of which is protected by a protective group, with various bromoacetylpyridine derivatives E. The reaction is shown in the following reaction formula (3).

Reaction formula (3):

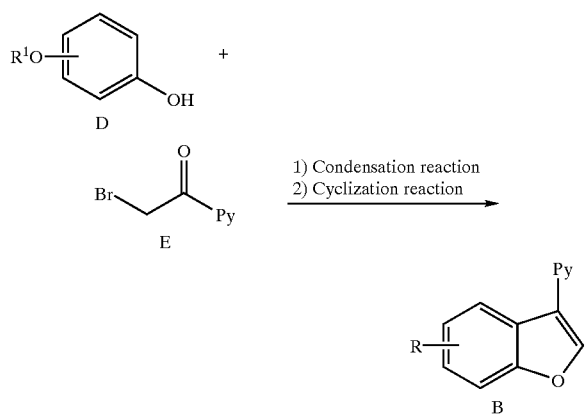

Compound B is converted into compound C by a deprotecting reaction. Then, after converting compound C into a triflate, the objective compound (I) is prepared by a cross-coupling reaction using various types of aryl boronic acid, aryl boronic acid ester, or borane derivative. Furthermore, the objective compound (I) can also be obtained by modifying a substituent on the phenyl group or aromatic heterocyclic group shown as R, if necessary.

In the reactions shown by the above three chemical reaction formulae (1)–(3), the raw material compound and the intermediates may be either a free compound or a salt, similar to the compound (I). In addition, the reaction mixture may be subjected to the reaction either as is or after isolation according to a conventional method. Regarding the compounds or derivatives thereof provided for the reactions, the amino group, carboxyl group, and hydroxyl group not involved in the reactions may be protected using protective groups. Known methods, such as that described in "PROTECTIVE GROUPS in ORGANIC SYNTHESIS" by T. W. Greene, P. G. M. Wuts, published by Wiley-Interscience (1999), and methods conforming to this method, may be applied to the addition and removal of the protective groups. As said protective group, an ether or ester of methyl, methoxymethyl, ethyl, 1-ethoxyethyl, phenacyl, tetrahydropyranylbenzyl, and the like; a silyl ether or ester of trimethylsilyl, t-butyldimethylsilyl, and the like; an ester or amide of formic acid, acetic acid, and the like; and a carbonate or carbamate of benzyloxycarbonyl, t-butyloxycarbonyl, and the like can be used.

Usually, an organic solvent not affecting the reaction is used as a solvent. Examples of organic solvents not adversely affecting the reaction are: saturated hydrocarbons such as hexane, pentane and the like; amides such as N,N-dimethylformamide (DMF), N,N-dimethylacetamide and the like; halogenated hydrocarbons such as dichloromethane, chloroform and the like; ethers such as diethyl ether, dioxane, tetrahydrofuran (THF) and the like; esters such as methyl acetate, ethyl acetate and the like; alcohols such as methanol, ethanol, 1-propanol, 2-propanol, 2-methyl-2- propanol, 1-butanol and the like; nitriles such as acetonitrile, propionitrile and the like; nitroalkanes such as nitromethane, nitroethane and the like; and aromatic hydrocarbons such as benzene, toluene, pyridine and the like. These solvents may be used either individually or in combination of two or more at an appropriate proportion.

When a base is used in the condensation reaction, triflatization reaction, and cross-coupling reaction, such base, for example, may include an alkali metal base such as lithium hydroxide, sodium hydroxide, potassium hydroxide, lithium carbonate, sodium carbonate, potassium carbonate, cesium carbonate, sodium hydrogen carbonate, potassium hydrogen carbonate, trisodium phosphate, tripotassium phosphate, sodium acetate, and potassium acetate; an alkali metal hydride such as sodium hydride, potassium halide; an amine such as diisopropylethyl amine, 2,6-lutidine, 2,6-di-t-butylpyridine, 2,6-di-t-butyl-4-methylpyridine, and triethylamine; and the like.

When an acid is used in the cyclization reaction, such acid, for example, may include a mineral acid such as hydrochloric acid, hydrobromic acid, sulfuric acid, phosphoric acid, and polyphospholic acid; an organic acid such as trifluoroacetic acid, p-toluene sulfonic acid, and methanesulfonic acid; Lewis acid such as zinc chloride, tin chloride, boron trifluoride diethyl ether complex, aluminium chloride, and titanium tetrachloride; and the like.

Example transition metal catalysts used in the cross-coupling reaction (indicating homo or hetero nuclear bond-formation reaction represented as Heck reaction, Suzuki reaction, Ullmann reaction and the like, for example) are palladium, nickel, or copper, each having 0 to 2 valence. These metals may form a complex with triphenylphosphine, dibenzylidene acetone, bis-diphenyl phosphinoferrocene, and the like. The cross-coupling reaction is usually carried out at a temperature of −80 to 200° C., and preferably 0 to 100° C., for usually about 5 minutes to about 5 days, and preferably 30 minutes to 2 days.

The compounds and the salt thereof of the present invention can be orally or parenterally administered safely to human beings and animals as pharmaceuticals. Suitable means for parenteral administration are intravenous injection, intramuscular injection, hypodermic injection, intraperitoneal injection, percutaneous (transdermal) administration, transpulmonary administration, pernasal administration, transintestinal administration, intraoral administration, transmucosal administration, and the like. Preparations for these purposes are used. Specific examples of the preparations may include injection, suppositories, aerosol agents, percutaneous absorption tapes, and the like.

Oral administration preparations include, for example, tablets (including sugar-coated tablets, coated tablets, buccal tablets), powder, capsules (including soft capsules), granules (including coated granules), pilules, troches, and liquid preparations, as well as their pharmaceutically acceptable sustained release preparations. Liquid preparations for oral administration include a suspension, emulsion, syrup, (including a dry syrup), and elixir.

These preparations are formulated according to known methods of making pharmaceutical preparations using pharmaceutically acceptable carriers, vehicles (excipients), disintegrators, lubricants, coloring agents, and the like for dosing as a pharmaceutical composition. Example carriers and vehicles used in these preparations are lactose, glucose, saccharose, mannitol, potato starch, cornstarch, calcium carbonate, calcium phosphate, calcium sulfate, crystalline cellulose, powdered glycyrrhiza, and powdered gentian. Example binders are starch, Tragacanth rubber, gelatin, syrup, polyvinyl alcohol, polyvinyl ether, polyvinyl pyrrolidone, hydroxypropyl cellulose, methylcellulose, ethyl cellulose, and carboxymethyl cellulose. Suitable disintegrator are starch, agar, gelatin powder, sodium carboxymethyl cellulose, calcium carboxymethyl cellulose, crystalline cellulose, calcium carbonate, sodium hydrogen carbonate, and sodium alginate. Example lubricants are magnesium stearate, talc, hydrogenated vegetable oils, macrogol, and the like. As coloring agents, any pharmaceutically acceptable coloring agents may be used.

Tablets and granules may be optionally coated with saccharose, gelatin, purified shellac, glycerol, sorbitol, ethyl cellulose, hydroxypropyl cellulose, hydroxypropylmethyl cellulose, polyvinyl pyrrolidone, phthalic acid cellulose acetate, hydroxypropylmethyl cellulose phthalate, methyl methacrylate, methacrylic acid polymer, and the like. These coating agents may be used either individually or in combination of two or more. Capsules made of a compound such as ethyl cellulose and gelatin—may also be used. When preparing a composition for injection, a pH adjusting agent, buffer agent, stabilizer, solubilizer, and the like, may optionally be added to the base component according to conventional methods.

When the compound of the present invention is administered to a patient, the dose varies depending on the conditions such as degree of symptom, age of the patient, health conditions, and body weight. A daily dose per adult for oral or non-oral administration may be in the range of 1–1000 mg, preferably 50–200 mg, and once or more per day, but not limited to this range.

EXAMPLES

The present invention will now be described in more detail by way of examples, which are given for the purpose of explanation and should not be construed as limiting the present invention.

Example 1

Preparation of 3-[6-(4-methoxyphenyl)benzo[b] furan-3-yl] Pyridine t-butyldimethylchlorosilane (3.6 g, 23.88 mmol) was added to a solution of 6-hydroxy-2,3-dihydrobenzo[b]furan-3-one (3.0 g, 19.98 mmol) and imidazole (2.0 g, 29.38 mmol) in N,N-dimethylformamide (DMF) (30 ml) under cooling with ice. The mixture was warmed to room temperature and stirred for 40 minutes. The reaction mixture was concentrated under reduced pressure. The resulting residue was diluted with ethyl acetate, washed with water, with diluted hydrochloric acid, with saturated aqueous solution of sodium bicarbonate, and then with saturated brine (aqueous solution of sodium chloride), sequentially, and dried with anhydrous magnesium sulfate. The solvent was evaporated under reduced pressure. The oily residue obtained was charged to silica gel column chromatography (hexane:ether=3:1) to obtain a yellow waxy product of 6-t-butyldimethylsilyloxy-2,3- dihydrobenzo[b]furan-3-one (4.3 g, 82%).

$^1$H-NMR (CDCl$_3$) δ: 0.24(s, 6H), 0.97(s, 9H), 4.59(s, 2H), 6.49(d, J=1.8 Hz, 1H), 6.54(dd, J=1.8, 8.5 Hz, 1H), 7.52(d, J=8.5 Hz, 1H).

Anhydrous trifluoromethane sulfonic acid (Tf$_2$O)(4.5 ml, 26.75 mmol) was added to a solution of 6-t-butyldimethylsilyloxy -2,3-dihydrobenzo[b]furan-3-one (6.6 g, 25.04 mmol) obtained above and 2,6-lutidine (3.3 ml, 28.33 mmol) in methylenechloride (120 ml) under cooling with ice. The mixture was warmed to room temperature and stirred for 30 minutes. The reaction mixture was concentrated under reduced pressure. The resulting residue was diluted with ether, washed with water, 5% citric acid aqueous solution, saturated aqueous solution of sodium bicarbonate, and then saturated brine solution, sequentially, and dried with anhydrous magnesium sulfate. The solvent was then evaporated under reduced pressure. The resulting oily residue was charged to silica gel column chromatography (hexane:ether=1:1) to obtain a yellow oily product of 6-t-butyldimethyl silyloxybenzo[b]furan-3-yl= trifluoromethane sulfonate (8.9 g, 89%).

$^1$H-NMR (CDCl$_3$) δ: 0.21(s, 6H), 0.98(s, 9H), 6.87(dd, J=1.8, 8.6 Hz, 1H), 6.94(d, J=1.8 Hz, 1H), 7.40(d, J=8.6 Hz, 1H), 7.70(s, 1H).

2M sodium carbonate aqueous solution (45 ml) was added to a solution of 6-t-butyldimethylsilyloxybenzo[b]-furan-3-yl- trifluoromethane sulfonate (8.9 g, 22.37 mmol) obtained above, diethyl (3-pyridyl) borane (4.0 g, 27.97 mmol), and bistriphenyl-phosphine palladium (II) chloride (1.6 g, 2.237 mmol) in THF (120 ml). The mixture was stirred for 2 hours at 80° C. The reaction mixture was concentrated under reduced pressure and the residue was diluted with ether. Insoluble material was removed by filtration through Celite® (trademark, Wako Pure Chemical Industries, Ltd.). After the water layer was removed from the filtrate, the filtrate was washed with water, then with saturated brine, and dried with anhydrous magnesium sulfate, followed by evaporating the solvent under reduced pressure. The resulting oily residue was charged to silica gel column chromatography (hexane:ether=1:1) to obtain a yellow oily product of 3-(6-t-butyldimethyl silyloxybenzo[b] furan-3-yl) pyridine (5.2 g, 71%).

$^1$H-NMR (CDCl$_3$) δ: 0.22(s, 6H), 1.00(s, 9H), 6.86(dd, J=2.4, 8.5 Hz, 1H), 7.02(d, J=1.8 Hz, 1H), 7.37(dd, J=4.9, 7.9 Hz, 1H), 7.58(d, J=8.5 Hz, 1H), 7.74(s, 1H), 7.90(dt, J=1.8, 7.9 Hz, 1H), 8.58(dd, J=1.8, 4.9 Hz, 1H), 8.88(d, J=2.4 Hz, 1H).

1M tetrabutylammonium fluoride solution in THF (16 ml, 16.00 mmol) was added to a THF (150 ml) solution of 3-(6-t-butyldimethyl silyloxybenzo[b]furan-3-yl)pyridine (5.2 g, 15.88 mmol) obtained above, and the mixture was stirred for 30 minutes at room temperature. The reaction mixture was concentrated under reduced pressure and the resulting concentrate was charged to short path silica gel column chromatography (chloroform:ethyl acetate= 1:1–1:2). A white powder of 3-(3- pyridyl)benzo[b]furan-6-ol (2.7g, 79%) was then obtained by crystallization using ether-hexane.

¹H-NMR (DMSO-d₆) δ: 6.86(dd, J=2.4, 8.6 Hz, 1H), 6.99(d, J=1.8 Hz, 1H), 7.50(dd, J=4.9, 7.9 Hz, 1H), 7.70(d, J=8.5 Hz, 1H), 8.10(dt, J=1.8, 7.9 Hz, 1H), 8.29(s, 1H), 8.55(dd, J=1.8, 4.9 Hz, 1H), 8.92(d, J=2.4 Hz, 1H), 9.69(s, 1H).

Melting point: 167–168° C.

Tf₂O (0.90 ml, 5.350 mmol) was added to a pyridine (20 ml) solution of 3-(3-pyridyl)benzo[b]furan-6-ol (1.0 g, 4.734 mmol) obtained above while cooling with ice. After increasing the temperature to room temperature, the mixture was stirred for 2 hours. The reaction mixture was concentrated under reduced pressure. The resulting residue was diluted with ethyl acetate, washed with saturated aqueous solution of sodium bicarbonate, water, and then saturated brine, sequentially, and dried with anhydrous magnesium sulfate, followed by evaporating the solvent under reduced pressure. The residue was purified by crystallization using ether-hexane to obtain a white powder of 3-(3-pyridyl)benzo[b]furan-6-yl=trifluoromethane sulfonate (1.5 g, 90%).

¹H-NMR (CDCl₃) δ: 7.27(dd, J=2.4, 8.6 Hz, 1H), 7.41 (ddd, J=1.2, 4.9, 7.9 Hz, 1H), 7.53(d, J=1.8 Hz, 1H), 7.80(d, J=8.6 Hz, 1H), 7.89(ddd, J=1.8, 2.4, 7.9 Hz, 1H), 7.92(s, 1H), 8.64(dd, J=1.8, 4.9 Hz, 1H), 8.86(d, J=2.4 Hz, 1H).

Melting point: 87.5–88° C.

Tetrakistriphenylphosphine palladium (0) (3.5 mg, 0.003029 mmol) was added to a suspension of 3-(3-pyridyl)benzo[b]furan-6-yl=trifluoromethane sulfonate (40 mg, 0.1165 mmol), 4-methoxyphenyl boronic acid (20 mg, 0.1316 mmol), and tripotassium phosphate (37 mg, 0.1743 mmol) in THF (5.0 ml). The mixture was stirred for 2 days at 80° C., then cooled to room temperature. After the addition of 2 M sodium hydroxide aqueous solution (0.075 ml) and 30% hydrogen peroxide aqueous solution (0.050 ml), the mixture was stirred for 1 hour at the same temperature. After diluting the reaction mixture with ether, the mixture was washed with water, then with saturated brine, and dried with anhydrous magnesium sulfate, followed by evaporating the solvent under reduced pressure. The residue was charged to silica gel column chromatography (hexane:ether=1:1). A white powder of 3-[6-(4-methoxyphenyl)benzo[b]furan-3-yl]pyridine (18 mg, 51%) was obtained by recrystallization using ethyl acetate-hexane.

¹H-NMR (CDCl₃) δ: 3.85(s, 3H), 7.00(d, J=9.2 Hz, 2H), 7.41(dd, J=1.8, 7.9 Hz, 1H), 7.58(d, 9.2 Hz, 2H), 7.72(d, J=1.8 Hz, 1H), 7.80(d, J=8.5 Hz, 1H), 7.85(s, 1H), 7.95(dt, J=1.8, 7.9 Hz, 1H), 8.61(dd, J=1.8, 4.9 Hz, 1H), 8.93(d, J=1.8 Hz, 1H).

IR (KBr): 2834, 1608, 1524, 1481, 1438, 1255, 807 cm⁻¹.

Melting point: 126–127° C.

Example 2

Preparation of 4-[3-(3-pyridyl)benzo[b]furan-6-yl] phenol

4-[3-(3-pyridyl)benzo[b]furan-6-yl]phenol (7.5 mg, 18%) was obtained from 3-(3-pyridyl)benzo[b]furan-6-yl=trifluoro- methane sulfonate (50 mg) in the same manner as in Example 1.

¹H-NMR (DMSO-d₆) δ: 6.86(d, J=8.5 Hz, 1H), 7.54(dd, J=4.9, 7.9 Hz, 1H), 7.58–7.61(m, 3H), 7.88(s, 1H), 7.95(d, J=8.5 Hz, 1H), 8.18 (m, 1H), 8.50(s, 1H), 8.59(m, 1H), 8.99(d, J=1.8 Hz, 1H), 9.58(s, 1H).

IR (KBr): 3100-2400, 1611, 1582, 1522, 1476, 1283, 1098, 808 cm⁻¹.

Melting point: 232.5–234.5° C.

Example 3

Preparation of 3-[6-(4-fluorophenyl)benzo[b]furan-3-yl] Pyridine 2M sodium carbonate aqueous solution (0.30 ml) was added to a solution of 3-(3-pyridyl)benzo[b]furan-6-yl=trifluoro methane sulfonate (50 mg, 0.1457 mmol) obtained in Example 1, 4-fluorophenyl boronic acid (27 g, 0.1930 mmol), and bistriphenylphosphine palladium (II) chloride (5.0 mg, 0.007123 mmol) in THF (120 ml). The mixture was stirred for 3 hours at 80° C. The reaction mixture was concentrated under reduced pressure. The resulting residue was diluted with ethyl acetate. The organic layer washed with water, then with saturated brine, and dried with anhydrous magnesium sulfate, followed by evaporating the solvent under reduced pressure. The residue obtained was charged to silica gel column chromatography (hexane:ethyl acetate=1:1). A white powder of 3-[6-(4-fluorophenyl)benzo[b]furan-3-yl]pyridine (29 mg, 69%) was obtained by crystallization using ether-hexane.

¹H-NMR (CDCl₃) δ: 7.15(t, J=9.2 Hz, 2H), 7.42(dd, J=4.9, 7.9 Hz, 1H), 7.52(dd, J=1.8, 8.5 hz, 1H), 7.60(dd, J=5.5, 9.2 Hz, 2H), 7.72 (m, 1H), 7.82(d, J=8.5 Hz, 1H), 7.86(s, 1h), 7.95(dt, J=1.8, 7.9 Hz, 1H), 8.62(dd, J=1.8, 4.9 Hz, 1H), 8.93(d, J=1.8 Hz, 1H).

IR (KBr): 1596, 1518, 1473, 1437, 1322, 1223, 1100, 810 cm⁻¹.

Melting point: 129.5–131° C.

Example 4

Preparation of 3-[6-(3-fluorophenyl)benzo[b]furan-3-yl] Pyridine

3-[6-(3-fluorophenyl)benzo[b]furan-3-yl]pyridine (43 mg, 51%) was obtained from 3-(3-pyridyl)benzo[b]furan-6-yl=trifluoromethane sulfonate (80 mg) in the same manner as in Example 3.

¹H-NMR (CDCl₃) δ: 7.04(m, 1H), 7.34(m, 1H), 7.40–7.43(m, 3H), 7.55(dd, J=1.8, 8.5 hz, 1H), 7.76(d, J=1.2 Hz, 1H), 7.84(d, J=8.5 Hz, 1H), 7.88(s, 1H), 7.95(dt, J=1.8, 7.9 Hz, 1H), 8.62(dd, J=1.2, 4.9 Hz, 1H), 8.93(d, J=1.8 Hz, 1H).

IR(KBr): 1611, 1563, 1477, 1411, 1311, 816 cm¹.

Melting point: 94.5–95.5° C.

Example 5

Preparation of 3-[6-(3-methoxyphenyl)benzo[b]furan-3-yl]pyridine

3-[6-(3-methoxyphenyl)benzo[b]furan-3-yl]pyridine (27 mg, 62%) was obtained from 3-(3-pyridyl)benzo[b]furan-6-yl=trifluoromethane sulfonate (50 mg) in the same manner as in Example 3.

¹H-NMR (CDCl₃) δ: 3.88(s, 3H), 6.91(dd, J=2.4, 7.9 Hz, 1H), 7.18(m, 1H), 7.23(m, 1H), 7.38(d, J=7.9 Hz, 1H), 7.40(dd, J=4.9, 7.9 Hz, 1H), 7.57(dd, J=1.2, 7.9 Hz, 1H), 7.77(d, J=1.8 Hz, 1H), 7.82(d, J=7.9 Hz, 1H), 7.86(s, 1H), 7.95(dt, J=2.4, 7.3 Hz, 1H), 8.61(dd, J=1.2, 4.9 Hz, 1H), 8.93(d, J=2.4 Hz, 1H).

IR (KBr): 2836, 1605, 1564, 1473, 1421, 1285, 1226, 781 cm⁻¹.

Melting point: 114.5–115° C.

Example 6

Preparation of 3-[3-(3-pyridyl)benzo[b]furan-6-yl] phenylamine

3-[3-(3-pyridyl)benzo[b]furan-6-yl]phenylamine (29 mg, 35%) was obtained from 3-(3-pyridyl)benzo[b]furan-6-yl=trifluoromethane sulfonate (80 mg) in the same manner as in Example 3.

$^1$H-NMR (CDCl$_3$) δ: 6.69(dd, J=2.4, 7.9 Hz, 1H), 6.96(t, J=1.8 Hz, 1H), 7.04(m, 1H), 7.24(m, 1H), 7.40(dd, J=4.9, 7.9 Hz, 1H), 7.55(dd, J=1.2, 7.9 Hz, 1H), 7.74(d, J=1.2 Hz,), 7.80(d, J=8.5 Hz, 1H), 7.85(s, 1H), 7.95(dt, J=1.8, 7.9 Hz, 1H), 8.62(dd, J=1.2, 4.9 Hz, 1H), 8.92(d, J=2.4 Hz, 1H).

IR (KBr): 3430, 1600, 1564, 1474, 1426, 782 cm$^{-1}$.

Melting point: 145–147° C.

Example 7

Preparation of 3-[6-(3-pyridyl)benzo[b]furan-3-yl]pyridine

3-[6-(3-pyridyl)benzo[b]furan-3-yl]pyridine (31 mg, 79%) was obtained from 3-(3-pyridyl)benzo[b]furan-6-yl=trifluoro methane sulfonate (50 mg) in the same manner as in Example 3.

$^1$H-NMR (CDCl$_3$) δ: 7.38(dd, J=4.9, 7.9 Hz, 1H), 7.41 (dd, J=4.9, 7.9 Hz, 1H), 7.56(dd, J=1.2, 7.9 Hz, 1H), 7.77(d, J=1.2 Hz, 1H), 7.87(d, J=7.9 Hz, 1H), 7.89(s, 1H), 7.94(m, 2H), 8.60(dd, J=1.2, 4.9 Hz, 1H), 8.62(dd, J=1.2, 4.9 Hz, 1H), 8.91(d, J=1.8 Hz, 1H), 8.93(d, J=1.8 Hz, 1H).

IR (KBr): 1586, 1562, 1472, 1438, 1418, 1402, 1329, 1079, 794 cm$^{-1}$.

Melting point: 140.5–141.5° C., Mass: 273 (M+H)

Example 8

Preparation of 3-[6-(1 3-benzodioxol-5-yl)benzo[b]furan3-yl] Pyridine

3-[6-(1,3-benzodioxole-5-yl)benzo[b]furan-3-yl]pyridine (269 mg, 84%) was obtained from 3-(3-pyridyl)benzo[b]furan-6-yl=trifluoromethane sulfonate (350 mg) in the same manner as in Example 3.

$^1$H-NMR (CDCl$_3$) δ: 6.00(s, 2H), 6.89(d, J=8.5 Hz, 1H), 7.10–7.12(m, 2H), 7.40(dd, J=4.9, 7.9 Hz, 1H), 7.50(dd, J=1.8, 8.5 Hz, 1H), 7.68(d, J=1.2 Hz, 1H), 7.79(d, J=8.5 Hz, 1H), 7.84(s, 1H), 7.94(dt, J=1.8, 7.9 Hz, 1H), 8.61(dd, J=1.8, 4.9 Hz, 1H), 8.92(d, J=1.8 Hz, 1H). p1 IR (KBr): 2897, 2793, 1510, 1471, 1432, 1229, 1035, 801 cm$^{-1}$.

Melting point: 143.5–144.5° C.

Example 9

Preparation of 3-(6-phenylbenzo[b]furan-3-yl)pyridine 3-(6-phenylbenzo[b]furan-3-yl)pyridine (21 mg, 53%) was obtained from 3-(3-pyridyl)benzo[b]furan-6-yl=trifluoromethane sulfonate (50 mg) in the same manner as in Example 3.

$^1$H-NMR (CDCl$_3$) δ: 7.35–7.48(m, 5H), 7.57(dd, J=1.8, 8.6 Hz, 1H), 7.65(d, J=8.6 Hz, 1H), 7.78(m, 1H), 7.87(s, 1H), 7.97(dt, J=1.8, 7.9 Hz, 1H), 8.65(dd, J=1.8, 4.9 Hz, 1H), 8.97(d, J=1.8 Hz, 1H).

IR (KBr): 1600, 1563, 1473, 1449, 1414, 1356, 1097, 965, 827 cm$^{-1}$.

Melting point: 91–92° C.

Example 10

Preparation of 3-[6-(3,4-dimethoxyphenyl)benzo[b]furan3-yl] Pyridine

3-[6-(3,4-dimethoxyphenyl)benzo[b]furan-3-yl]pyridine (207 mg, 72%) was obtained from 3-(3-pyridyl)benzo[b]furan- 6-yl=trifluoromethane sulfonate (300 mg) in the same manner as in Example 3.

$^1$H-NMR (CDCl$_3$) δ: 3.93(s, 3H), 3.96(s, 3H), 6.96(d, J=8.5 Hz, 1H), 7.16(d, J=2.4 Hz, 1 H), 7.20(dd, J=1.8, 7.9 Hz, 1H), 7.41(dd, J=4.9, 7.9 Hz, 1H), 7.54(dd, J=1.2, 7.9 Hz, 1H), 7.73(d, J=1.2 Hz, 1H), 7.80(d, J=8.5 Hz, 1H), 7.85(s, 1H), 7.95(dt, J=1.8, 7.9 Hz, 1H), 8.61(dd, J=1.2, 4.9 Hz, 1H), 8.93(d, J=1.8 Hz, 1H).

IR (KBr): 2837, 1601, 1527, 1486, 1442, 1411, 1254, 1141, 1023 cm$^{-1}$.

Melting point: 138.5–139.5° C.

Example 11

Preparation of 3-[3-(3-pyridyl)benzo[b]furan-6-yl]phenol

47% hydrobromic acid solution (1.6 ml) was added to 3-[6-(3-methoxyphenyl)benzo[b]furan-3-yl]pyridine (80 mg, 0.2655 mmol) obtained in Example 5, and the mixture was refluxed for 24 hours. After neutralizing with 2N sodium hydroxide aqueous solution and a saturated aqueous solution of sodium bicarbonate, and extracting with ethyl acetate, the organic layer was washed with water, then with saturated brine, and dried with anhydrous magnesium sulfate, followed by evaporating the solvent under reduced pressure. The product was crystallized in ether-chloroform to obtain a white powder of 3-[3-(3-pyridyl)benzo [b]furan-6-yl]phenol (58 mg, 76%).

$^1$H-NMR (DMSO-d$_6$) δ: 6.78(dd, J=2.4, 7.9 Hz, 1H), 7.11(dd, J=1.8, 2.4 Hz, 1H), 7.16(d, J=7.9 Hz, 1H), 7.27(t, J=7.9 Hz, 1H), 7.55(dd, J=3.6, 7.9 Hz, 1H), 7.61(dd, J=1.8, 8.6 Hz, 1H), 7.91(d, J=1.2 Hz, 1H), 7.99(d, J=8.6 Hz, 1H), 8.19(dt, J=1.8, 8.5 Hz, 1H), 8.59(dd, J=1.8, 8.5 Hz, 1H), 9.00(d, J=1.8 Hz, 1H), 9.55(s, 1H).

IR (KBr): 3200-2400, 1586, 1565, 1509, 1473, 1295, 1220, 1104, 966, 809 cm$^1$.

Melting point: 205–207° C.

Example 12

Preparation of 4-[3-(3-pyridyl)benzo[b]furan-6-yl]-1,2-benzenediol hydrobromide

47% hydrobromic acid solution (1.6 ml) was added to 3-[6-(3,4-dimethoxyphenyl)benzo[b]furan-3-yl]pyridine (80 mg, 0.2414 mmol) obtained in Example 10, and the mixture was refluxed for 12 hours. The precipitate was filtered to obtain a pale yellow powder of 4-[3-(3-pyridyl)benzo[b]furan-6-yl]-1,2- benzenediol hydrobromide (76 mg, 82%)

$^1$H-NMR (DMSO-d$_6$) δ: 6.84(d, J=7.9 Hz, 1H), 7.05(dd, J=2.4, 7.9 Hz, 1H), 7.14(d, j=2.4 Hz, 1H), 7.60(dd, J=1.8, 8.5 Hz, 1H), 7.85(d, J=1.8 Hz, 1H), 8.02–8.04(m, 2H), 8.70(s, 1H), 8.80(br d, J=6.7 Hz, 1H), 8.84(d, J=4.9 Hz, 1H), 9.26(s, 1H).

IR (KBr): 3300–2400, 1595, 1573, 1534, 1491, 1419, 1221, 799 cm$^{-1}$.

Melting point: 280° C. and more than 280° C.

Example 13

Preparation of 3-[6-(3-thienyl)benzo[b]furan-3-yl]pyridine hydrochloride 2M aqueous solution of sodium carbonate (0.45 ml) was added to a solution of 3-(3-pyridyl)benzo[b]furan-6-yl=trifluoromethane sulfonate (100 mg, 0.2913 mmol) obtained in Example 1, thiophene-3-boronic acid (50 mg, 0.3907 mmol), and bistriphenylphosphine palladium (II) chloride (10 mg, 0.01425 mmol) in THF (4 ml). The mixture was stirred for 2 hours at 80° C. The reaction mixture was concentrated under reduced pressure and the residue was diluted with ether. Insoluble material was removed by filtration through Celite® (Wako Pure Chemical Industries, Ltd.). After removing the water layer from the filtrate, 2N hydrochloric acid solution was added to the filtrate to form a precipitate. The precipitate was filtered to obtain a white powder of 3-[6-(3-thienyl) benzo[b]furan-3-yl]pyridine hydrochloride (73 mg, 80%).

$^1$H-NMR (DMSO-d$_6$) δ: 7.67(dd, J=3.1 Hz, 1H), 7.70(dd, J=1.8, 5.5 Hz, 1H), 7.81(dd, J=1.2, 8.5 Hz, 1H), 8.01–8.05 (m, 3H), 8.11(d, J=1.2 Hz, 1H), 8.73(s, 1H), 8.79(m, 1H), 8.82d, J=5.5 Hz, 1H), 9.26(d, J=1.8 Hz, 1H).

IR (KBr): 3466, 3067, 2615, 1581, 1473, 1436, 783 cm$^{-1}$.

Melting point: 214.5–215° C.

Example 14

The Measurement of Steroid 17α-hydroxylase and/ or Steroid C17-20 Lyase Inhibitory Activity An experiment was carried out according to the method of T. Sergejew and R. W.

Hartmann (J. Enzyme Inhibition, 8, 113 (1994)). That is, the testis of rats (SD, male) was homogenized and centrifuged to obtain microsome. Each compound of the present invention prepared in Examples 1–13 was put into a micro tube (1.5 ml, Eppendorf Co.). After the addition of 100 µl of microsome protein solution, the concentration of which was adjusted to 0.1 mg/ml using 50 mM phosphate buffer solution (pH 7.4), 140 µl of 125 nmol NADPH solution, and 10 µl of 6.25 nmol 17α-hydroxyprogesterone, the mixture was incubated at 37° C. for 20 minutes. 50 µl of 1N hydrochloric acid and 1000 µl of ethyl acetate were sequentially added to the mixture. The mixture was shaken and centrifuged. The ethyl acetate layer was then washed with 250 µl of 50 mM phosphate buffer solution (pH 7.4) and 50 µl of IN hydrochloric acid, centrifuged, and concentrated. The concentrate was dissolved in 100 µl of acetonitrile. 10 µl of this solution was charged to high performance liquid chromatography. The amounts of the substrate and the formed product (androstenedione and testosterone) were measured to determine the enzyme activity. A sample without the test compound added was provided as a control. Steroid 17α-hydroxylase and/or steroid C17-20 lyase inhibitory activity (%) was calculated from the amounts of each substrate and product using the following equation (1). The results are shown in Table 1.

$$\text{Inhibitory activity}(\%) = 100 - \frac{\text{Enzymatic activity with test compound}}{\text{Enzymatic activity without test compound}} \times 100 \quad (1)$$

TABLE 1

| Example | Inhibitory activity (%) |
|---------|-------------------------|
| 3 | 64 |
| 4 | 45 |
| 6 | 90 |
| 7 | 75 |
| 9 | 45 |
| 11 | 81 |

TABLE 1-continued

| Example | Inhibitory activity (%) |
|---------|-------------------------|
| 12 | 66 |
| 13 | 89 |

Source enzyme: Rat testis microsome
Test compound concentration: 300 nM
Substrate concentration: 25 µM (17 α-hydroxyprogesterone)
NADPH concentration: 500 µM Industrial Applicability Novel benzofuran derivatives are provided by the present invention.

The compounds of the present invention exhibit potent inhibitory activity of steroid 17α-hydroxylase and/or steroid C 17-20 lyase. They also inhibit aromatase.

The compounds of the present invention are therefore useful as preventive and/or therapeutic agents for various diseases depending upon androgenic hormones and estrogens, such as prostate cancer, prostatic hypertrophy (prostatism), androgenic syndrome (masculinization), andromorphous baldness, breast cancer, mastopathy, uterine cancer, endometrosis, and ovarian cancer.

What is claimed is:

1. A benzofuran derivative represented by the following formula (I), or salt thereof:

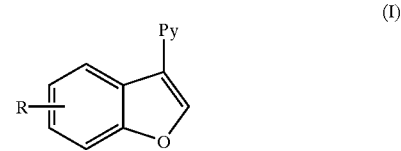

(I)

wherein Py is selected from the group consisting of 2-pyridyl, 3-pyridyl, and 4-pyridyl;

R is selected from the group consisting of a phenyl, a substituted phenyl, a pyridyl, and a thienyl; wherein when R is substituted phenyl the substituent is selected from the group consisting of hydroxyl, C1–C7 alkyloxy, methylenedioxo, halogen atom, and amino.

2. A benzofuran derivatives or salt thereof as claimed in claim 1; wherein R is substituted phenyl and the substituent is selected from the group consisting of a hydroxyl, a methoxyl, a fluorine atom, and an amino.

3. A benzofuran derivative or the salt as claimed in claim 1, wherein R is a benzodioxole group.

4. A benzofuran derivative or the salt thereof as claimed in claim 1, wherein said benzofuran derivative is selected from the group consisting of 3-[6-(4-methoxyphenyl)benzo [b]furan 3yl]pyridine, 4-[3-(3-pyridyl)benzo[b]furan-6-yl] phenol, 3-[6-(4-fluorophenyl)benzo[b]furan-3-yl]pyridine, 3-[6-(3-fluorophenyl)benzo[b]furan-3-yl]pyridine, 3-[6-(3-methoxyphenyl)benzo[b]furan-3-yl]pyridine, 3-[3-(3-pyridyl)benzo[b]furan-6-yl]phenylamine, 3-[6-(3-pyridyl) benzo[b]furan-3-yl]pyridine, 3-[6-(1,3-benzodioxole-5-yl) benzo[b]furan-3-yl]pyridine, 3-(6-phenylbenzo[b]furan-3-yl)pyridine, 3-[6-(3,4-dimethoxyphenyl)benzo[b]furan-3-yl]pyridine, 3-[3-(3-pyridyl)benzo[b]furan-6-yl]phenol, 4-[3-(3-pyridyl)benzo[b]furan-6-yl]-1,2-benzenediol, and 3-[6-(3-thienyl)benzo[b]furan-3-yl]pyridine.

5. A benzofuran derivative or the salt thereof as claimed in claim 1, wherein said benzofuran derivative is selected from the group consisting of 3-[3-(3-pyridyl)benzo[b]furan-6-yl]phenylamine, 3-[6-(3-pyridyl)benzo[b]furan-3-yl]

pyridine, 3-[3-(3-pyridyl)benzo[b]furan-6-yl]phenol, and 3-[6-(3-thienyl)benzo[b]furan-3-yl]pyridine.

6. A benzofuran derivative or the salt thereof as claimed in claim 1, wherein said benzofuran derivative is selected from the group consisting of 3-[6-(4-fluorophenyl)benzo[b]furan-3-yl]pyridine, 3-[6-(3-fluorophenyl)benzo[b]furan-3-yl]pyridine, 3-(6-phenylbenzo[b]furan-3-yl)pyridine, and 4-[3-(3-pyridyl)benzo[b]furan-6-yl]-1,2-benzenediol.

7. A benzofuran derivative or the salt thereof as claimed in claim 1, wherein said benzofuran derivative is selected from the group consisting of 3-[6-(4-methoxyphenyl)benzo[b]furan-3-yl]pyridine, 4-[3-(3-pyridyl)benzo[b]furan-6-yl]phenol, 3-[6-(3-methoxyphenyl)benzo[b]furan-3-yl]pyridine, 3-[6-(1,3-benzodioxole-5-yl)benzo[b]furan-3-yl]pyridine, and 3-[6-(3,4-dimethoxyphenyl)benzo[b]furan-3-yl]pyridine.

8. A composition, comprising:
a physiologically acceptable medium and the benzofuran derivative or salt thereof as claimed in claim 1.

9. A composition, comprising:
a physiologically acceptable medium and the benzofuran derivative or salt thereof as claimed in claim 2.

10. A composition, comprising:
a physiologically acceptable medium and the benzofuran derivative or salt thereof as claimed in claim 3.

11. A composition, comprising:
a physiologically acceptable medium and the benzofuran derivative or salt thereof as claimed in claim 4.

12. A composition, comprising:
a physiologically acceptable medium and the benzofuran derivative or salt thereof as claimed in claim 5.

13. A composition, comprising:
a physiologically acceptable medium and the benzofuran derivative or salt thereof as claimed in claims 6.

14. A composition, comprising:
a physiologically acceptable medium and the benzofuran derivative or salt thereof as claimed in claim 7.

15. A method of reducing steroid 17 α-hydroxylase activity in a mammal, comprising:
administering to a mammal in need thereof the pharmaceutical composition of claim 8 in an amount effective for educing steroid 17 α-hydroxylase activity; wherein said reducing of steroid 17 α-hydroxylase activity is relative to the steroid 17 α-hydroxylase activity in the absence of the pharmaceutical composition.

16. A method of reducing steroid C17-20 lyase activity in a mammal, comprising:
administering to mammal in need thereof the pharmaceutical composition of claim 8 in an amount effective for reducing steroid C17-20 lyase activity; wherein said reducing of steroid C17-20 lyase activity is relative to the steroid C17-20 lyase activity in the absence of the pharmaceutical composition.

17. A method of treating a disease selected from the group consisting of prostate cancer, prostatic hypertrophy, androgenic syndrome, andromorphous baldness, breast cancer, mastopathy, uterine cancer, endometriosis, and ovarian cancer, comprising:
administering to a mammal in need thereof an effective amount of the pharmaceutical composition of claim 8.

* * * * *